United States Patent [19]

Doshi et al.

[11] Patent Number: 5,012,037

[45] Date of Patent: Apr. 30, 1991

[54] INTEGRATED THERMAL SWING-PRESSURE SWING ADSORPTION PROCESS FOR HYDROGEN AND HYDROCARBON RECOVERY

[75] Inventors: Kishore J. Doshi, Somers; Michael J. Mitariten, Peekskill, both of N.Y.; Michael Whysall, Wilrijk, Belgium

[73] Assignee: UOP, Des Plaines, Ill.

[21] Appl. No.: 463,315

[22] Filed: Jan. 10, 1990

[51] Int. Cl.$^5$ .............................................. C07C 7/12
[52] U.S. Cl. .................................. 585/822; 585/820; 585/826; 208/310 R; 208/310 Z; 208/99; 208/103; 55/25; 55/26; 55/31; 55/33
[58] Field of Search ............ 585/820, 822, 826; 208/310 R, 310 Z, 99, 103; 55/25, 26, 31, 33

[56] References Cited

U.S. PATENT DOCUMENTS

| | | | |
|---|---|---|---|
| 3,069,349 | 12/1962 | Meiners | 585/820 |
| 3,430,418 | 3/1969 | Wagner | 55/25 |
| 3,738,084 | 6/1973 | Simonet et al. | 55/31 |
| 3,841,058 | 10/1974 | Templeman | 55/33 |
| 3,884,830 | 5/1975 | Grant | 208/310 R |
| 3,986,849 | 10/1976 | Fuderer et al. | 55/25 |
| 4,058,452 | 11/1977 | Loboda | 208/134 |
| 4,249,915 | 2/1981 | Sircar et al. | 55/26 |
| 4,404,118 | 9/1983 | Henskovits | 585/826 |
| 4,484,933 | 11/1984 | Cohen | 55/25 |
| 4,547,205 | 10/1985 | Steacy | 55/25 |
| 4,645,516 | 2/1987 | Doshi | 55/16 |
| 4,769,047 | 9/1988 | Dye | 585/822 |
| 4,813,980 | 3/1989 | Sircar | 55/26 |

*Primary Examiner*—Curtis R. Davis
*Assistant Examiner*—Nhat Phan
*Attorney, Agent, or Firm*—Thomas K. McBride; John G. Tolomei

[57] ABSTRACT

Processes are disclosed for the separation of light hydrocarbons from a feedstream containing hydrogen, light hydrocarbons and heavy hydrocarbons. The processes employ thermal swing adsorption zone to adsorb heavy hydrocarbons and a pressure swing adsorption zone to remove the remaining light hydrocarbons. At least a portion of the product from the pressure swing adsorption zone is used to purge the thermal swing adsorption zone. Specific applications of the process of the present invention are disclosed with relation to hydrodealkylation processes and dehydrocyclodimerization processes.

39 Claims, 3 Drawing Sheets

INTEGRATED THERMAL SWING-PRESSURE SWING ADSORPTION PROCESS FOR HYDROGEN AND HYDROCARBON RECOVERY

FIELD OF THE INVENTION

The present invention relates to adsorption process and more particularly to integrated processes employing thermal swing and pressure swing adsorption for separating light hydrocarbons from mixtures thereof with hydrogen and heavy hydrocarbons.

BACKGROUND OF THE INVENTION

Hydrocarbon conversion processes are often performed in the presence of hydrogen. This is done for various reasons such as to aid the vaporization of the hydrocarbon, to provide hydrogen which is necessary for the desired reaction or to prolong the life of catalyst used in the reaction zone. In many cases, the hydrogen is recovered from the reaction zone effluent and recirculated. Often this recycle hydrogen stream is purified before being returned to the reaction zone. In another mode of operation the hydrogen is not recycled, or if recycled it is only after having passed through other processing units or purification steps. This is most commonly practiced in processes which consume only minor amounts of hydrogen or which produce hydrogen. These include, for example, isomerization processes, alkylation and dealkylation processes, hydrogenation and dehydrogenation processes, reforming processes and mild desulfurization or denitrification processes.

It is not uncommon for hydrocarbon conversion processes to produce effluents which need to be thereafter separated into hydrocarbon products. Frequently, hydrocarbon conversion processes produce light hydrocarbons as by-products which need to be removed from the process to avoid a buildup. While it is possible to purge the system to remove light hydrocarbons, such action can be undesirable due to the loss of desired components along with the by-products. Hence, it is often desired to separate light hydrocarbons, e.g., $C_4-$, from heavier hydrocarbons, e.g., $C_5+$, and hydrogen, e.g., from a purge stream or from a reactor effluent separator overhead stream. This type of separation is required, for example, in the thermal dealkylation of alkylaromatic hydrocarbons, such as for the production of benzene from toluene. Toluene is produced in large quantities, often as the by-product of thermal cracking, extraction, reforming or isomerization operations, or directly from petroleum or coal derived naphtha fractions. However, the market for toluene can be limited, and there is a significant economic incentive for its conversion to benzene since benzene is in demand as a basic starting material in the production of many petrochemicals. A variety of separation techniques for performing such separations have been proposed.

U.S. Pat. No. 4,058,452, issued to Laboda, relates to the dealkylation of aromatic hydrocarbons and discloses a process wherein a hydrogen-containing feedstream stream is purified in an absorber to remove light paraffins and produce a hydrogen-rich gas stream which is passed through the reaction zone on a once-through basis. The gas separated from the reaction zone effluent by partial condensation is passed into a stripper as the stripping media used to remove these same light paraffins from the liquid used in the absorber.

A similar type of separation is disclosed in U.S. Pat. No. 4,547,205, issued to Steacy, which sets forth processes for the recovery of hydrogen and $C_6+$ product hydrocarbons from the effluent stream of a hydrocarbon conversion reaction zone. The effluent stream is partially condensed to remove the bulk of the heavy hydrocarbons, which are sent to a fractionation zone. The remaining vapor is compressed to a substantially higher pressure. The vapor then passes into an autorefrigeration zone in which it is cooled and partially condensed by indirect heat exchange against flashed fluids. The still pressurized uncondensed compounds are transferred to a pressure swing adsorption zone, which produces a high purity hydrogen product.

As noted in the above cited U.S. Pat. No. 4,547,205 one stage in the separation process is performed using pressure swing adsorption. Both thermal swing adsorption processes and pressure swing adsorption processes are generally known in the art for various types of adsorptive separations. Generally, thermal swing processes utilize the process steps of adsorption at a low temperature, regeneration at an elevated temperature with a hot purge gas and subsequent cooling down to the adsorption temperature. One process for drying gases generally exemplary of thermal swing processes is described in U.S. Pat. No. 4,484,933, issued to Cohen. The patent describes basic thermal swing processing steps coupled with the use of an auxiliary adsorber bed for improving the regeneration step. Thermal swing processes are often used for drying gases and liquids and for purification where trace impurities are to be removed. Often, thermal swing processes are employed when the components to be adsorbed are strongly adsorbed on the adsorbent, i.e., water, and thus, heat is required for regeneration.

Pressure swing adsorption (PSA) provides a means for adsorption that does not require heat for regeneration. Instead, regeneration is accomplished by reducing the pressure in the adsorber bed to below the pressure at which adsorption had occured. PSA process typically include the steps of adsorption at an elevated pressure, desorption to a lower pressure and repressurization to the adsorption pressure. The process also often include a purge step at the desorption pressure to enhance desorption.

Such PSA processing is disclosed in U.S. Pat. No. 3,430,418 issued to Wagner and in U.S. Pat. No. 3,986,849 issued to Fuderer et al., wherein cycles based on the use of multi-bed systems are described in detail. As is generally known and described in these patents, the contents of which are incorporated herein by reference as if set out in full, the PSA process is generally carried out in a sequential processing cycle that includes each bed of the PSA system. Such cycles are commonly based on the release of void space gas from the product end of each bed in one or more cocurrent depressurization steps upon completion of the adsorption step. In these cycles, the released gas typically is employed for pressure equalization and for subsequent purge steps. The bed is thereafter countercurrently depressurized and often purged to desorb the more selectively adsorbed component of the gas mixture from the adsorbent and to remove such gas from the feed end of the bed prior to the repressurization thereof to the adsorption pressure.

PSA processes have been employed for both purification and bulk separations. Some PSA processes such as set forth in the above-described U.S. Pat. No. 3,430,418 are particularly well suited for providing a single high purity product gas such as hydrogen and a waste, or fuel gas. Other PSA processes have been disclosed to recover more than one product quality gas. This is often desired when there are two or more desired components in the feedstream.

A PSA process is disclosed in U.S. Pat. No. 4,813,980, issued to Sicar, which relates to the separation of hydrogen, and carbon dioxide from mixtures with methane and other light gases and utilizes two groups of adsorber beds connected in series. The adsorbers in the first group undergo a cycle sequence comprising the following steps, (a) adsorption, (b) high pressure rinse, i.e., copurge, (c) depressure, (d) evacuation, i.e, vacuum, (e) equalize pressure, and (f) final pressurization. The adsorbers in the second group undergo a cycle sequence comprising the following steps (1) adsorption, (2) pressure equalization, (3) depressurizing, (4) purge, and (5) repressurization. The above-identified process can be severely deficient when separating feedstreams that contain heavy hydrocarbons because of the difficulty in desorbing heavy hydrocarbons by pressure swing methods.

Combined thermal swing-pressure swing processes have been proposed for dehydration and carbon dioxide removal, particularly in the purification of air and natural gas streams. U.S. Pat. No. 3,738,084, issued to Simonet, et al., discloses a process for the adsorption of moisture and carbon dioxide that employs thermal swing adsorption in one adsorber and both pressure swing and thermal swing in another adsorber. U.S. Pat. No. 3,841,058, issued to Templeman, discloses a method of purifying natural gas or the like to render it suitable for liquefaction. The method consists essentially of absorbing water and methanol from a natural gas stream also containing carbon dioxide in a first bed of absorbent material and subsequently absorbing carbon dioxide in a second bed of absorbent material, regenerating the absorbent material of the first bed by passing gas therethrough at an elevated temperature and regenerating the absorbent material in the second bed by pressure reduction at a temperature not exceeding 100° C. U.S. Pat. No. 4,249,915, issued to Sicar, et al., discloses a process employing both thermal swing and pressure swing adsorption to remove moisture and carbon dioxide from air. The patent discloses that the air stream is passed to the pressure swing adsorber to remove moisture and the effluent therefrom is passed to the thermal swing adsorber to remove carbon dioxide.

Although integrated thermal swing-pressure swing processes have been proposed for air and light gas purification, there is no specific direction in the disclosures of these processes of how to separate light hydrocarbons from mixtures with hydrogen and heavy hydrocarbons. Accordingly, in view of the above-described need to separate light hydrocarbons from mixture with hydrogen and heavy hydrocarbons, processes are sought which can utilize thermal swing and pressure swing adsorption technology to accomplish the desired separation.

SUMMARY OF THE INVENTION

A process is provided for the separation of light hydrocarbons from mixtures with hydrogen and heavy hydrocarbons that itilize an integrated thermal swing-pressure swing process. Heavy hydrocarbons are initially adsorbed in the thermal swing adsorber and light hydrocarbons are subsequently adsorbe in the pressure swing adsorber. Hydrogen, which is removed as an effluent from the pressure swing adsorber, is used as a purge gas in desorbing heavy hydrocarbons from the thermal swing adsorber to provide a product stream containing hydrogen and heavy hydrocarbons.

In one aspect of the present invention, there is provided an integrated thermal swing-pressure swing adsorption process for separating light hydrocarbons from a feedstream containing mixtures thereof with hydrogen and heavy hydrocarbons. The process includes the steps of: (a) passing the feedstream through a first adsorption zone containing solid adsorbent at a temperature and pressure sufficient to adsorb at least a portion of the heavy hydrocarbons and withdrawing a first adsorption effluent stream comprising hydrogen and light hydrocarbons and having a reduced amount of heavy hydrocabons relative to the feedstream; (b) passing the first adsorption effluent stream through a second adsorption zone containing solid adsorbent at a temperature and pressure sufficient to adsorb at least a portion of the light hydrocarbons and withdrawing a second adsorption effluent stream comprising hydrogen and having a reduced amount of light hydrocarbons relative to the first adsorption effluent stream; (c) heating at least a portion of the second adsorption effluent stream to a temperature sufficient to desorb at least a portion of the heavy hydrocarbons, passing the heated portion to said first adsorption zone and withdrawing a first desorption effluent stream comprising the heavy hydrocarbons; (d) reducing the pressure in the second adsorption zone to a pressure sufficient to desorb at least a portion of the light hydrocarbons therefrom and withdrawing a second desorption effluent comprising the light hydrocarbons.

In another specific aspect of the present invention, there is provided a process for separating an effluent stream from a hydrocarbon conversion process containing hydrogen, $C_1$–$C_5$ hydrocarbons and $C_6+$ hydrocarbons. The process includes the steps of: (a) cooling the effluent stream to a temperature sufficient to condense a portion thereof and provide a liquid condensate stream comprising a $C_6+$ hydrocarbon fraction and a vapor overhead stream comprising hydrogen, a $C_1$–$C_5$ hydrocarbon fraction and a $C_6+$ hydrocarbon fraction; (b) passing the vapor overhead stream through a first adsorption zone containing solid adsorbent at a temperature and pressure sufficient to adsorb at least a portion of the $C_6+$ hydrocarbon fraction and withdrawing a first adsorption effluent stream containing hydrogen and the $C_1$–$C_5$ hydrocarbon fraction and having a reduced amount of the $C_6+$ hydrocarbon fraction relative to the vapor overhead stream; (c) passing the first adsorption effluent stream through a second adsorption zone containing solid adsorbent at a pressure sufficient to adsorb at least a portion of the $C_1$–$C_5$ hydrocarbon fraction and withdrawing a second adsorption efluent stream comprising hydrogen and having a reduced amount of the $C_1$–$C_5$ hydrocarbon fraction relative to the first adsorption effluent stream; (d) heating at least a portion of the second adsorption effluent to a temperature sufficient to desorb $C_6+$ hydrocarbons, passing the heated portion to said first adsorption zone and withdrawing a first desorption effluent stream containing at least a portion of the $C_6+$ hydrocarbon fraction; (e) reducing the pressure in the second adsorption zone to a pressure sufficient to desorb $C_1$–$C_5$ hydrocarbons therefrom and withdrawing a second desorption effluent containing at least a portion of the $C_1$-$C_5$ hydrocarbon fraction.

DETAILED DESCRIPTION OF THE INVENTION

Figure 1:
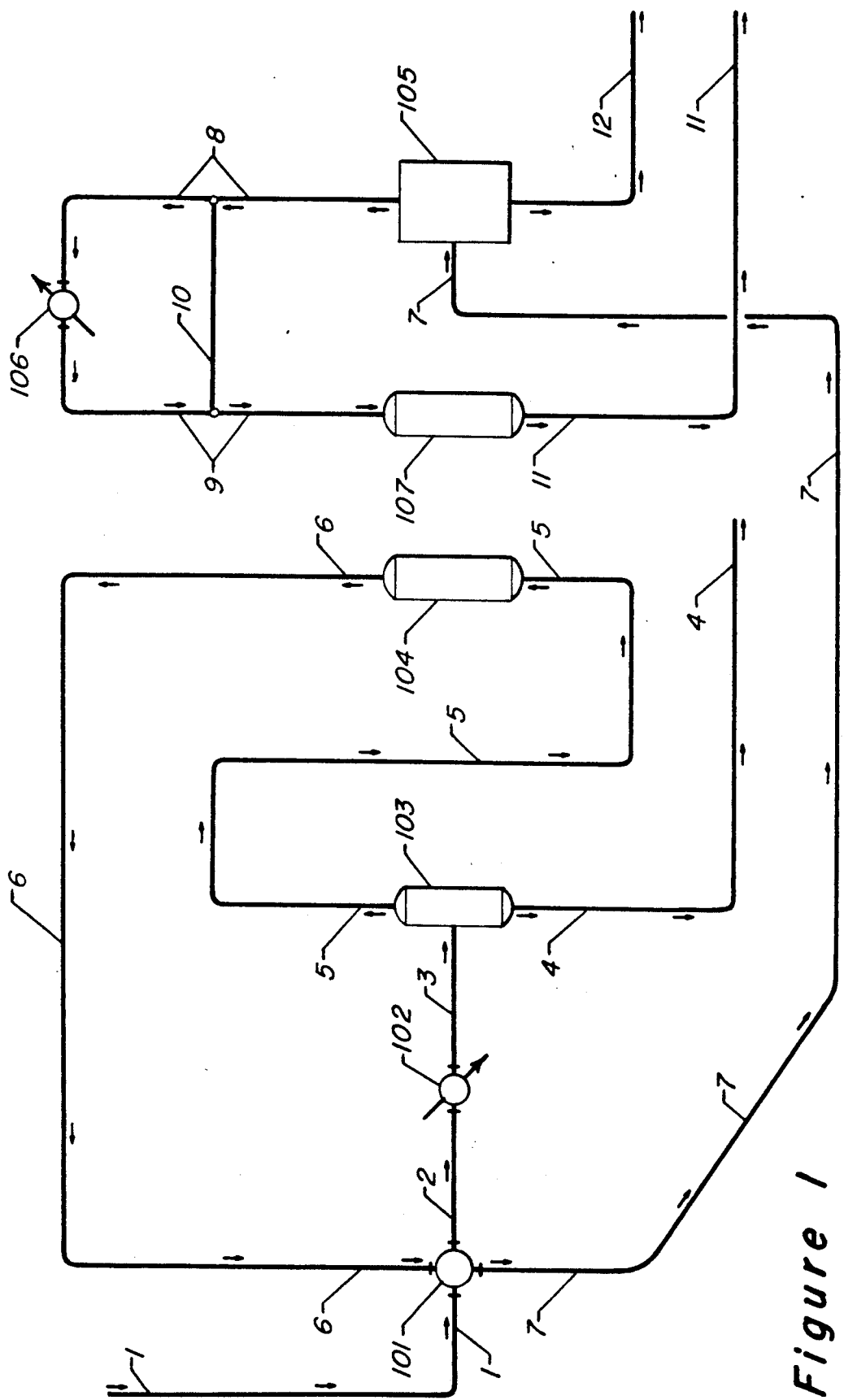
FIG. 1 illustrates a flowscheme utilizing the process of the present invention.

The process of the present invention is intended to be practiced on feedstreams comprising hydrogen, light hydrocarbons and heavy hydrocarbons. The term "light hydrocarbons" is intended to include hydrocarbons having from 1 to about 4 carbon atoms per molecule. The term "heavy hydrocarbons" is intended to include hydrocarbons having from about 6 to 20 carbon atoms per molecule, preferably from about 6 to 12 carbon atoms per molecule and most preferably from about 6 to 9 carbon atoms per molecule. Depending upon the particular application, hydrocarbons having 5 carbon atoms per molecule can be classified as either being light or heavy hydrocarbons. It is to be understood that although in general, heavy hydrocarbons are adsorbed in the thermal swing adsorber, i.e., first adsorption, zone and light hydrocarbons are adsorbed in the pressure swing adsorber, i.e., second adsorption zone, there may be instances when it is desired to adsorb some light hydrocarbons in the thermal swing adsorber or some heavy hydrocarbons in the pressure swing adsorber. Also, as is known by those skilled in the art, there is expected to be a certain amount of co-adsorption of the species, particular evident is the co-adsorption of light hydrocarbons in the thermal swing adsorber along with heavy hydrocarbons.

The relative amount of each feedstream component is not critial to performing the process of the present invention. Generally, however, it is desirable to have enough hydrogen to efficiently desorb heavy hydrocarbons from the thermal swing adsorber. Preferably, the molar ratio of hydrogen to heavy hydrocrbon will be at least one, more preferably at least five and most preferably at least ten. However, when necessary, lesser amounts of hydrogen can be employed and compensated for by increasing the adsorbent inventory in the thermal swing adsorber or increasing the desorption temperature. Such adjustments are known to those skilled in the art and need not be further discussed herein. Typically, the feedstream will be cooled and partially condensed before entering the thermal swing adsorber to remove some of the heavy hydrocarbons. Such partially condensed feedstreams will typically contain less than about 5 mol.% heavy hydrocarbons. A typical feedstream composition suitable for treatment according to the process of the present invention would contain from about 1 to 20 mol.% heavy hydrocarbons, 10 to 70 mol.% light hydrocarbons and 20 to 90 mol.% hydrogen.

The process of the present invention can be carried out using any suitable adsorbent material in the first and second adsorption zones having the desired selectivity for the light and heavy hydrocarbons in the feedstream. Suitable adsorbents known in the art and commercially available include crystalline molecular sieves, activated carbons, activated clays, silica gels, activated aluminas and the like. The molecular sieves include, for example, the various forms of silicoaluminophosphates, and aluminophosphates disclosed in U.S. Pat. No. 4,440,871; 4,310,440 and 4,567,027, hereby incorporated by reference as well as zeolitic molecular sieves.

Zeolitic molecular sieves in the calcined form may be represented by the gneral formula;

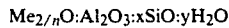

$Me_{2/n}O:Al_2O_3:xSiO:yH_2O$ where Me is a cation, x has a value from about 2 to infinity, n is the cation valence and y has a value of from about 2 to 10.

Typical well-known zeolites which may be used include, chabazite, also referred to as Zeolite D, clinoptilolite, erionite, faujasite, also referred to as Zeolite X and Zeolite Y, ferrierite, mordenite, Zeolite A, and Zeolite P. Other zeolites suitable for use according to the present invention are those having a high silica content, i.e., those having silica to alumina ratios greater than 10 and typically greater than 100. One such high silica zeolite is silicalite, as the term used herein includes both the silicapolymorph disclosed in U.S. Pat. No. 4,061,724 and also the F-silicalite disclosed in U.S. Pat. No. 4,073,865, hereby incorporated by reference.

Detailed descriptions of source of the above identified zeolites may be found in D. W. Breck, ZEOLITE MOLECULAR SIEVES, John Wiley and Sons, New York, 1974, hereby incorporated by reference. The patents referred to in the Background of the Invention contain further information concerning the various known adsorbents used for thermal swing and PSA operations and suitable for use in the practice of the invention.

It is often desirable when using crystalline molecular sieves that the molecular sieve be agglomerated with a binder in order to ensure that the adsorbent will have suitable physical properties. Although there are a variety of synthetic and naturally occurring binder materials available such as metal oxides, clays, silicas, aluminas, silica-aluminas, silica-zirconias, silica-thorias, silica-berylias, silica-titanias, silica-alumina-thorias silica-alumina-zirconias, mixtures of these and the like, clay-type binders are preferred. Examples of clays which may be employed to agglomerate the molecular sieve without substantially altering the adsorptive properties of the zeolite are attapulgite, kaolin, volclay, sepiolite, polygorskite, kaolinite, bentonite, montmorillonite, illite and chlorite. The choice of a suitable binder and methods employed to agglomerate the molecular sieves are generally known to those skilled in the art and need not be further described herein.

In the first adsorption zone, there are at least two adsorber beds which are thermally cycled between adsorption and regneration steps. The temperatute and pressure conditions in the adsorption beds and elsewhere in the adsorption system are those generally found to be suitable in other thermal swing process schemes, taking into account the nature of the feedstream. During the adsorption stroke when the feedstream is being passed through a primary adsorber to selectively adsorb and remove heavy hydrocarbons, the temperature of the feedstream is generally kept below about 150° F. and preferably between about 0-100° F. and more preferably between about 40° to 100° F. in order to enhance the hydrocarbon loading. At temperatures below 40° F., solidifaction of certain hydrocarbons, e.g., benzene, can occur. Also pressure within the adsorber will preferably be at least one atmosphere and can advantageously be higher when the heavy hydrocarbon partial pressure of the feedstream is low, in order to increase the heavy hydrocarbon pressure over the adsorbent and increase the resulting heavy hydrocrbon loading. Preferably, the pressure in the first adsorption zone is in the range of from about 100 to 1000 psia. The degree of increase in pressure above one atmosphere and the temperature conditions are controlled with respect to each other with reference to the feedstream to maintain vapor phase operation with desired efficacy in the manner well known in the art.

During the regeneration of an adsorber bed in the first adsorption zone, the purge gas is typically heated to temperatures significantly higher than the temperature of the adsorbent mass in order to lower the equilibrium heavy hydrocarbon loading and facilitate desorption and purging of the heavy hydrocarbons (and other impurity adsorbates) from the bed. In general, the higher the purge gas temperature, the less quantity of purge gas required, although such factors as hydrothermal abuse of the adsorbent and higher heat energy losses due to untoward differentials between internal and external bed temperatures will be taken into account by those skilled in the art. For purposes of the present invention, it is preferred that the temperature is from about 100°-600° F. It is further preferred that the temperature be from about 100°-350° F. when the adsorbate is sufficiently desorbable in said temperature range. Otherwise, it is preferred that the temperature be from 300°-600° F. when the adsorbate is difficult to desorb. It is not necessary that the purge gas be heated over the entire period of hot purge regeneration, since the heat of the regenerated adsorbent mass at the ingress end of the bed during regeneration can be carried forward even with unheated incoming purge gas. Routing calculations can be readily made by those skilled in the art in view of any given process system to establish suitable process conditions. Those skilled in the art may also employ indirect heating methods, e.g., heating coils in beds instead of or in addition to the purge gas. After regeneration, the first adsorption zone is cooled to the adsorption temperature by methods which are well known to those skilled in the art, such as but not limited to, passing a cooling stream therethrough, e.g., cooled purge gas, or passing the feedstream therethrough. Optionally, the first adsorption zone may additionally be regenerated by reducing the pressure therein, i.e., PSA. Such a pressure reduction can be performed either before, after or simultaneously with the thermal regeneration.

The adsorption effluent from the first adsorption zone is passed to a second adsorption zone which comprises at least three adsorber vessels, each of which undergoes, on a cyclic basis, high pressure adsorption, optional cocurrent depressurization to intermediate pressure level(s) with release of void space gas from the product end of the bed, countercurrent depressurization to a lower desorption pressure with the release of desorbed gas from the feed end of the bed, with or without purge of the bed, and repressurization to higher adsorption pressure. Of course, the adsorption cycle in the second adsorption zone can comprise additional steps well known in PSA such as cocurrent depressurization steps or cocurrent displacement steps as are well known in the PSA art. It is to be understood that the term "countercurrent" denotes that the direction of gas flow through the adsorption zone, i.e., adsorber bed, is countercurrent with respect to the direction of feedstream gas flow. Similarly, the term "cocurrent" denotes flow in the same direction as the feedstream gas flow.

While the effluent from the first adsorption zone can be passed directly to the second adsorption zone, it is occasionally desirable to heat the effluent from the first adsorption zone by indirect heat exchange with the feedstream to the first adsorption zone thereby partially cooling the feedstream to the first adsorption zone. Such cooling of the feedstream to the first adsorption zone enhance the performances of the thermal swing cycle by increasing the delta temperature between adsorption and desorption. Preferably, the second adsorption zone is maintained in a pressure range of from about 100 to 1000 psia during adsorption and from about 14.7 to about 200 psia during countercurrent depressurization. When intermediate cocurrent depressurization steps or equalization steps are employed, the pressure at the end of said steps will be intermediate between the adsorption and countercurrent depressurization pressures. Preferably, the temperature in the second adsorption zone is from about 0°-120° F. throughout the pressure swing cycle although temperatures outside this range can be employed depending on the particular separation to be performed.

An important aspect of the thermal swing and the pressure swing processes of the present invention resides in the utilization of at least a portion of the adsorption effluent stream, preferably the entire effluent, from the second adsorption zone for purging the first adsorption zone. This configuration is especially useful when it is desired to remove light hydrocarbons from a feedstream comprising hydrogen, light hydrocarbons and heavy hydrocarbons. In addition to providing an effective means for regenerating the first adsorption zone, the use of the second zone adsorption effluent provides for recombining the hydrogen stream with the heavy hydrocarbons. Often in hydrocarbon processing, it is desired to reject the light hydrocarbon fraction, which may for example comprise cracked gases, etc., that would otherwise build up. However, it is to be understood that in some instances, the light gas fraction withdrawn from the process may be recovered as a desired stream.

The process of the present invention is hereinafter described with reference to the drawings which illustrate various aspects of the present invention. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation column overhead and reboiler systems, etc. It may also be readily discerned that the process flow presented in the drawings may be modified in many aspects without departing from the basic overall concept of the invention. For example, the number of heat exchangers shown in the drawings have been held to a minimum for purposes of simplicity. Those skilled in the art will recognize that the choice of heat exchange methods employed to obtain the necessary heating and cooling at various points within the processes subject to a large amount of variation as to how it is performed. Accordingly, there exists many possibilities for indirect heat exchange between different process streams. Depending on the specific location and circumstance of the installation of the subject process, it may also be desired to employ heat exchange against steam, hot oil, or process streams from other processing units not shown on the drawings.

FIG. 1 illustrates a process flowscheme that can be employed to separate light hydrocarbons, e.g., methane, from hydrogen and heavy hydrocarbons, e.g., benzene. Such a separation is desired in processes for the thermal hydrodealkylation (THDA) of toluene to produce benzene where hydrogen and toluene are passed to a thermal reactor to produce benzene and methane. U.S. Pat. No. 4,058,452 discloses processes for the dealkylation of alkylaromatic hydrocarbons and is hereby incorporated by reference. Often, there is significant purge of the hydrogen-and-methane-containing reactor effluent off-gas to avoid a build-up of methane. The process of the present invention can be employed to remove methane from this stream.

With reference to FIG. 1, a feedstream containing about 60 mol.% hydrogen, 2 mol.% benzene and 38 mol.% methane is passed via line 1 at a pressure of about 430 psia at a temperature of about 104° F. to a heat exchanger 101 wherein it is cooled to about 65° F. by indirect heat exchange with an adsorption effluent carried by a line 6, and passed a via line 2 to a chiller 102 wherein it is further cooled to about 40° F. The cooled feedstream is passed via a line 3 to a flash chamber 103 to provide a liquid phase comprising benzene passed via a line 4 and a vapor phase comprising hydrogen, methane and residual benzene passed via a line 5. The vapor phase is passed via line 5 to adsorber 104 in the first adsorption zone.

It is to be understood that it is not necessary to cool and flash the feedstream, i.e., line 1, prior to passing to the first adsorption zone. However, such cooling can be advantageous because it removes some of the benzene and hence reduces the size of the first adsorption zone wherein the adsorption of the removed benzene would otherwise occur. Further, it lowers the temperature of the feedstream to the first adsorption zone which can increase the temperature difference between adsorption and regeneration steps and effectively increase the capacity of the first adsorption zone.

The first adsorption zone contains at least two adsorber beds, i.e. adsorber beds 104 and 107, each containing a suitable adsorbent for adsorbing benzene, e.g., activated carbon, although those skilled in the art will recognize that more than two adsorber beds as well as more complicated adsorption cycles can be employed. A first zone adsorption effluent depleted in benzene is withdrawn from adsorber 104 via line 6 and passed to heat exchanger 101 as hereinbefore described where it is heated to about 94° F. before being passed to the a second adsorption zone 105 via a line 7. Optionally, the heating step can be omitted and the effluent from the first adsorption zone can be passed directly to the second zone.

The second adsorption zone contains at least three adsorber beds, and optionally more adsorber beds, containing a suitable adsorbent for adsorbing methane, e.g., activated carbon. A second zone adsorption effluent depleted in methane is removed via a line 8 and passed to a heat exchanger 106 wherein it is heated to a temperature of about 250° F. and passed via a line 9 to first zone adsorber 107 to heat and purge said adsorber 107 and desorb adsorbed benzene.

It is to be understood that adsorber 107 had been previously loaded with benzene in the manner described with respect to adsorber 104. The amount of benzene to be adsorbed in each adsorber can be determined by one skilled in the art depending upon the desired product purities. For example, in some instances, it may be desirable to permit some benzene to elute into the first zone adsorption effluent to ensure a high purity benzene product. In other instances, it may be desirable to stop the adsorption step prior to breakthrough of the benzene and retain a portion of the methane in the first adsorption zone. In such instances, one skilled in the art may employ a suitable combination of adsorbents to accomplish the desired result.

A product stream comprising hydrogen and benzene is withdrawn via a line 11 from adsorber 107. In a THDA process, for example, this stream can be recycled back to the THDA reactor without separation, utilized for further processing or the products can be separated by conventional means and the hydrogen can be recycled to the reactor. After the desorption of benzene has progressed for a period of time from adsorber 107, the second zone adsorption effluent is diverted around heat exchanger 106 via a line 10 in order to cool adsorber 107 down to about the second zone adsorption effluent temperature. During such cooling some additional desorption of benzene occurs. The determination of when to direct the purge gas around heat exchanger 106 for cooling adsorber 107 depends on process considerations known to those skilled in the art. Final cooling to the 40° F. adsorption temperature is accomplished by passing the cooled feedstream therethrough during the adsorption step.

Methane adsorbed in the adsorber beds in the second adsorption zone is desorbed by reducing the pressure to near atmospheric. A series of intermediate cocurrent depressurization and equalization steps is employed as desired in order to improved hydrogen recovery in the second adsoption zone prior to the final depressurization and purging steps. Such steps are known in the art and need not be discussed further herein.

Figure 2:
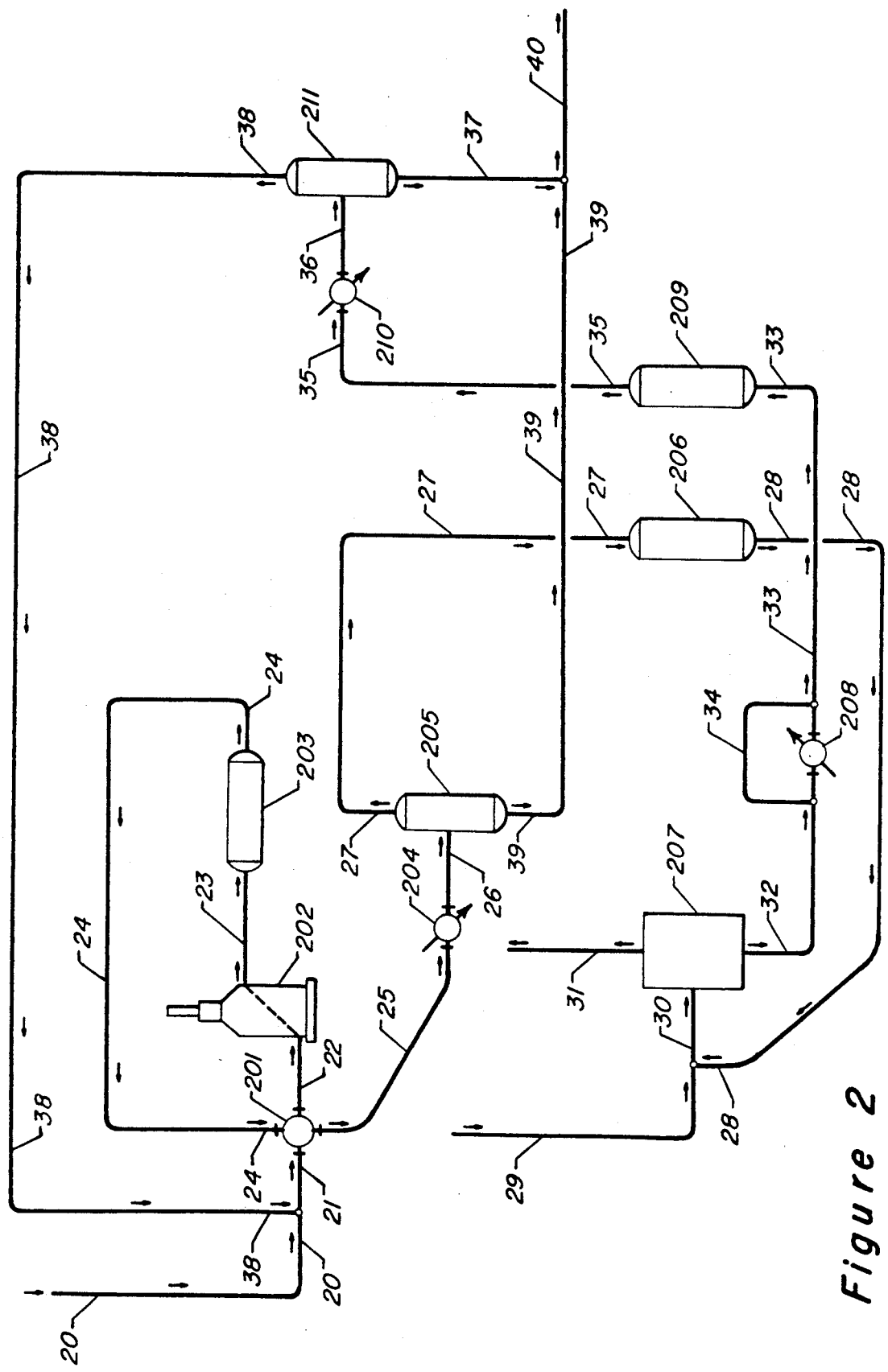
FIG. 2 illustrates the process of the present invention applied to a hydrogen consuming process.

FIG. 2 illustrates an integration of the process of the present invention into a deakylation process, e.g., thermal hydrodealkylation, such as disclosed in the above-mentioned U.S. Pat. No. 4,058,452. The configuration illustrated in FIG. 2 is particularly useful when the hydrogen feedstream contains light hydrocarbon impurities such as methane through butane. A feedstream comprising alkylaromatic hydrocarbon is introduced to the process via a line 20, combined with a hydrogen stream 38, the source of which is hereinafter defined, and passed to a heat exchanger 201 for preheating via a line 21. The preheated stream is passed via a line 22 to furnace 202 and then to reactor 203 via a line 23. The reaction system is described in above-mentioned U.S. Pat. No. 4,058,452.

Generally, when thermal hydrodealkylation is employed, the reactor preferably comprises a vertical cylindrical vessel having an inlet at the top. This vessel will not contain any material chosen or designed to operate as a catalyst. Nevertheless, the materials used withing the reactor may exhibit some catalytic activity at the high temperatures used within this zone. It is preferred that the upper one half to two thirds of the reaction zone be essentially empty and that the remaining portion of the zone contain a means for providing plug flow, such as inert ceramic balls, vertical baffles, etc. Thermal hydrodeakylation conditions generally include a temperature of from about 1100° to 1500° F. or higher and a pressure of from about 300 to 800 psig. The residence time of the feedstream within the reaction zone should be within the broad range of from about 4 to 60 seconds, with 12 to 30 seconds being a preferred range. A hydrogen to $C_6+$ hydrocarbon ratio of at least 2 and preferably 4 to 8 is maintained within the reaction zone. The reaction zone should be operated in a manner which limits the increase within the reaction zone to less than 200° F. and preferably within the range of from about 100° to 175° F.

In the catalytic hydrodeakylation of alkylaromatics, the preferred condition include a pressure of from about 300 to 1000 psig and a temperature of from about 900° to 1500° F. Essentially any catalyst capable of performing the desired reaction is suitable for use in accordance with the present invention. One suitable catalyst comprises an oxide of a metal of Group VI-B of the periodic Table such as chromium, molybdenum of tungsten on a refractory inorganic oxide, preferably alumina. Other metals which may be utilized on the catalyst include those classified in Group VIII of the Periodic Table, including platinum, nickel, iron and cobalt and also rhenium and manganese. A particularly preferred catalyst comprises chromium composited on a high surface area alumina with the chromium being present in an amount of 10 to 20 wt% of chromium oxide based on the alumina. The feedstream should be charged at a liquid hourly space velocity of from about 0.5 to about 5.0, with a hydrogen to hydrocarbon ratio of from about 5:1 to 15:1 being maintained in the reaction zone.

The reactor effluent is withdrawn via a line 24 and passed to heat exchanger 201 for partial cooling thereof and passed via a line 25 to heat exchanger 204 for further cooling thereof. The cooled reactor effluent is passed via a line 26 to a flash chamber 205 wherein a liquid aromatic product is withdrawn via a line 39 and a vapor phase comprising hydrogen, $C_1$-$C_4$ hydrocarbons, and aromatic hydrocarbons is withdrawn via a line 27. The vapor phase, i.e., line 27, is passed to a first zone adsorber 206 of a first adsorption zone wherein the aromatic hydrocarbons are adsorbed.

A first zone adsorption effluent comprising hydrogen and $C_1$-$C_4$ hydrocarbons is withdrawn via a line 28 and combined with an inpure hydrogen feedstream, by a line 29. The combined feedstream is passed via a line 30 to the second adsorption zone, i.e., PSA zone, wherein the feedstream is separated into a fuel gas stream containing $C_1$-$C_4$ hydrocarbons, i.e., a line 31, and a hydrogen product stream, i.e., by a line 32. The hydrogen product stream is passed to a heat exchanger 208 for heating to the desired desorption temperature and passed via a line 33 to adsorber 209 of the first adsorption zone which is undergoing desorption. A line 34 provides a bypass around heat exchanger 208 for cooling adsorbers 206 and 209. The desorption effluent stream from adsorber 209, which comprises hydrogen and aromatic hydrocarbons, is passed via a line 35 to condensor 210 and then in to a flash chamber 211 via a line 36. A liquid aromatic product is withdrawn via a line 37 and combined with a line 39 to form a product line 40. The overhead vapor is withdrawn via a line 38 and combined with the alkylaromatic feedstream, line 20, as hereinbefore described.

Figure 3:
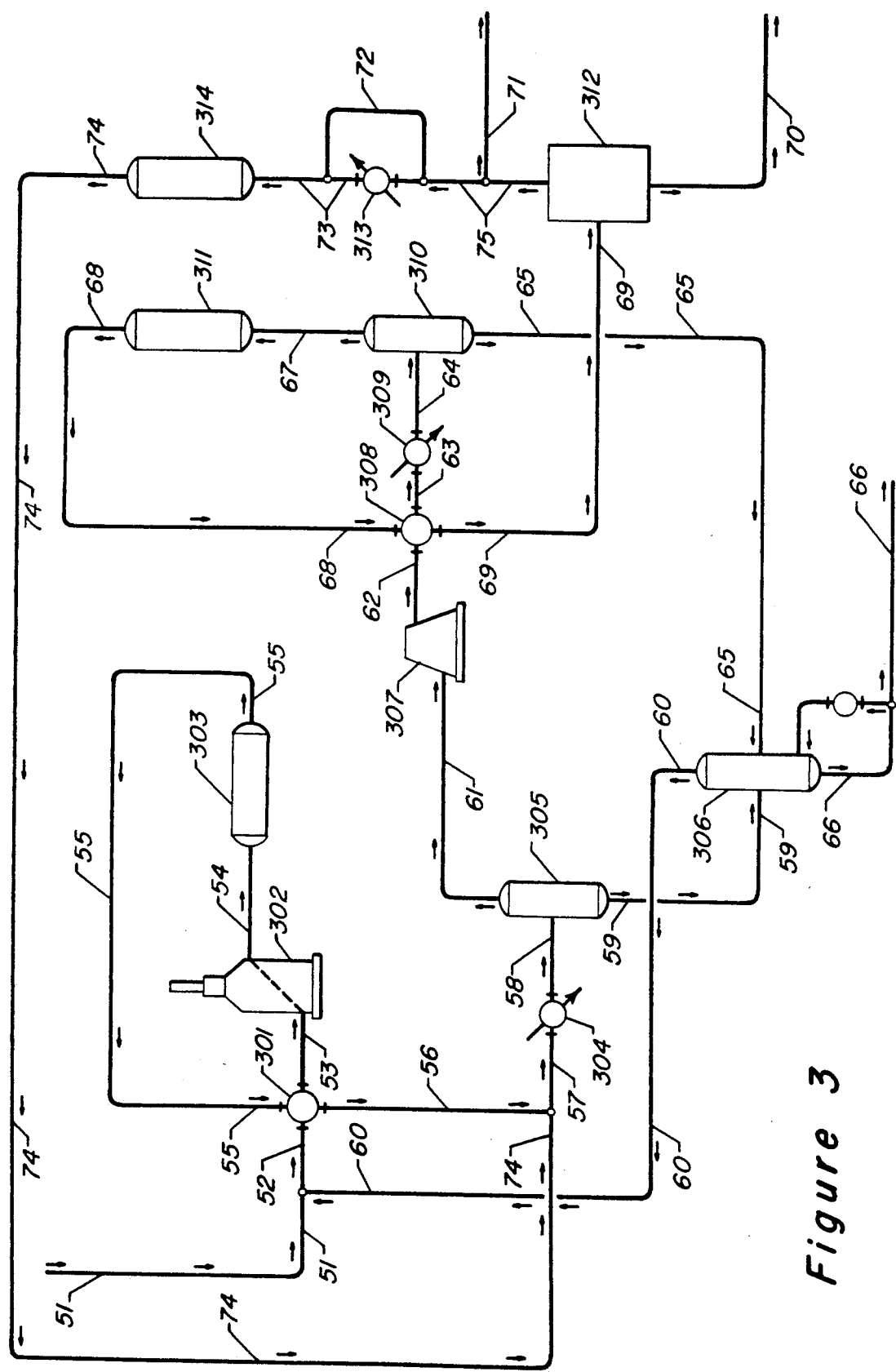
FIG. 3 illustrates the processes of the present invention applied to a hydrogen producing process.

FIG. 3 illustrates a flowscheme wherein the present invention is integrated with a process for the dehydrocyclodimerization of propane and butane containing feedstreams to produce a product containing aromatic hydrocarbons. A dehydrocyclodimerization process is disclosed in U.S. Pat. No. 4,547,205 which relates to processes for the recovery of hydrogen and $C_6+$ hydrocarbons from an effluent stream of a hydrocarbon conversion reaction zone and is hereby incorporated by reference.

With reference to FIG. 3, a feedstream comprising propane and butane is introduced to the process via a line 51 and combined with additional propane and butane from a line 60, the source of which is hereinafter defined. The combined stream is passed to a heat exchanger 301 via a line 52 and then to a furnace 302 via a line 53 to be heated. The heated stream is passed to a reactor 303 where via a line 54, the conversion takes place. The details of the reaction can be found in above-mentioned U.S. Pat. No. 4,547,205 hereby incorporated by reference.

Generally, the reactor system comprises a moving bed radial flow multi stage reactor such as described in U.S. Pat. Nos. 3,652,231, 3,692,496, 3,706,536, 3,785,963, 3,825,116, 3,839,196, 3,839,197, 3,854,887, 3,856,662, 3,918,930, 3,981,824, 4,094,814, 4,110,091, 4,403,909. These patents also describe catalyst regeneration systems and various aspects of moving catalyst bed operations and equipment. This reactor system has been widely employed commercially for the reforming of naphtha fractions. It has also been described for the dehydrogenation of light paraffins.

The preferred moving bed reactor system employs a spherical catalyst having a diameter of about 1/64 to 1/8 inch. The catalyst preferably comprises a support material and a metallic component deposited thereon. Currently, zeolitic supports are preferred and zeolite ZSM-5 is especially preferred. The preferred metallic component is gallium as described in U.S. Pat. No. 4,180,689. A dehydrocyclodimerization reaction zone is preferably operated at a temperature of from about 920° to 1050° F. and a pressure under 100 psig. Hydrogen producing reactions are normally favored by low pressures and pressures under 70 psig are especially preferred.

The reactor effluent which comprises aromatic hydrocarbons, hydrogen, methane, ethane, propane and butane, is passed via a line 55 to heat exchanger 301 wherein it is partially cooled. The partially cooled reactor effluent is combined by a line 56, with first zone desorption effluent, carried by a line 74, the source of which is hereinafter described, and passed via a line 57 to a condensor 304 and then to a flash chamber 305 via a line 58. A liquid phase is withdrawn via a line 59 and passed to a deisobutanizer column 306. The hydrocarbon product containing aromatic hydrocarbons is withdrawn via a line 66. The ovehead from the column 306, which comprises propane and butane, is recycled via a line 60 to be combined with feedstream 51.

The vapor phase from flash chamber 305 is withdrawn via a line 61 and passed to a compressor 307 where it is compressed to over 200 psia and passed via a line 62 to a heat exchanger 308 where it is partially cooled by indirect heat exchange with a first zone adsorption effluent, via a line 68, as hereinafter described. The partially cooled stream is passed via a line 63 to a cooler 309 and then via a line 64 to a flash chamber 310. A liquid phase comprising aromatic hydrocarbons, butane and propane is passed via a line 65 to debutanizer column 306. The vapor phase from flash chamber 310 is withdrawn via a line 67 and passed to an adsorber 311 undergoing adsorption in the first adsorption zone. Alternately, for example, the vapor phase from flash chamber 305, line 61 can be passed to adsorber 311 prior to compression.

The adsorption step in adsorber bed 311 is continued until a substantial portion of the methane, ethane and hydrogen has eluted from the bed but a substantial portion of propane and bustane is retained in the bed. At such a point, the adsorption step is terminated and the feedstream is directed to another adsorber in the first adsorption zone. The effluent from the first adsorption zone is passed via line 68 to heat exchanger 308 as hereinbefore described and thereafter passed via a line 69 to a second adsorption zone 312, i.e. PSA. A fuel gas stream comprising methane and ethane is withdrawn via a line 70. The second zone adsorption effluent stream is withdrawn via a line 75, and a portion thereof is withdrawn via a line 71 as product hydrogen. The remaining portion is passed through a heat exchanger 313 or alternately bypassed via a line 72 and passed via a line 73 to an adsorber 314 of the first adsorption zone which is undergoing desorption, i.e., TSA. The desorption effluent from adsorber 314 via line 74 is combined with line 56 as hereinbefore described. In some cases, instead of recycling the desorption effluent, i.e., line 74, to heat exchanger 304 and flash chamber 305, it may be desirable to separately recover the aromatic hydrocarbons to avoid the hydrogen recycle. Such variations are intended to be within the scope of the present invention.

It will be apparent to those skilled in the art that the process of the present invention can be utilized in processes other than described above. For example, in process for the conversion of synthetic gas to liquid motor fuels such as described in U.S. Pat. No. 4,579,834, it may be desired to separate light hydrocarbons in the $C_1$-$C_4$ range from heavy hydrocarbons in the $C_5+$ range and hydrogen. Also, in process for the conversion of methane to produce hydrocarbons and hydrogen such as described in U.S. Pat. No. 4,704,888, it may be desirable to separate the light hydrocarbons from the heavy hydrocarbons and hydrogen. Moreover, there are a number of other hydrocarbon conversion processes, such as the catalytic reforming of naphtha and the dehydrogenation of paraffins, for example, wherein the process of the present invention can be utilized within the scope of the claims that follow.

What is claimed is:

1. An integrated thermal swing-pressure swing adsorption process for separating light hydrocarbons from a feedstream containing hydrogen, light hydrocarbons and heavy hydrocarbons, said process comprising:
   (a) passing the feedstream through a first adsorption zone containing solid adsorbent at a temperature and pressure sufficient to adsorb at least a portion of the heavy hydrocarbons in said first adsorption zone and withdrawing a first adsorption effluent stream comprising hydrogen and light hydrocarbons;
   (b) passing the first adsorption effluent stream through a second adsorption zone containing solid adsorbent at a temperature and pressure sufficient to adsorb at least a portion of the light hydrocarbons in said second adsorption zone and withdrawing a second adsorption effluent stream comprising hydrogen;
   (c) heating at least a substantial portion of the second adsorption effluent stream to a temperature sufficient to desorb at least a portion of the heavy hydrocarbons, passing the heated portion to said first adsorption zone and withdrawing a first desorption effluent stream comprising the heavy hydrocarbons and hydrogen; and
   (d) reducing the pressure in the second adsorption zone to a pressure sufficient to desorb at least a portion of the light hydrocarbons therefrom and withdrawing a second desorption effluent comprising the light hydrocarbons.

2. The process of claim 1 wherein the temperature of said second adsorption zone during step (b) is higher than the temperature of said first adsorption zone during step (a).

3. The process of claim 1 which further comprises heating the first adsorption effluent stream prior to passing through said second adsorption zone.

4. The process of claim 3 wherein the first adsorption effluent stream is heated by indirect heat exchange with a process stream comprising said feed stream, said process stream being cooled by said indirect heat exchange.

5. The process of claim 4 which further comprises flashing said process stream subsequently to said indirect heat exchange to separate said process stream into a vapor fraction comprising the feedstream and a liquid fraction comprising heavy hydrocarbons.

6. The process of claim 5 which further comprises cooling said process stream after said heat exchange and prior to said flashing.

7. The process of claim 1 wherein the light hydrocarbons comprise hydrocarbons having from one to five carbon atoms per molecule and the heavy hydrocarbons comprise hydrocarbons having six or more carbon atoms per molecule.

8. The process of claim 1 which further comprises reducing the pressure in the first adsorption zone to desorb another portion of the heavy hydrocarbons either before, after or simultaneously with step (c).

9. A process for separating an effluent stream from a hydrocarbon conversion process containing hydrogen, $C_1$-$C_5$ hydrocarbons and $C_6+$ hydrocarbons, said process comprising:
   (a) cooling the effluent stream to a temperature sufficient to condense a portion thereof and provide a liquid condensate stream comprising a portion of the $C_6+$ hydrocarbons and a vapor overhead stream comprising hydrogen, a $C_1$-$C_5$ hydrocarbon fraction and a $C_6+$ hydrocarbon fraction;
   (b) passing the vapor overhead stream through a first adsorption zone containing solid adsorbent at a temperature and pressure sufficient to adsorb at least a portion of the $C_6+$ hydrocarbon fraction and withdrawing a first adsorption effluent stream comprising hydrogen and the $C_1$-$C_5$ hydrocarbon fraction;
   (c) passing the first adsorption effluent stream through a second adsorption zone containing solid adsorbent at a pressure sufficient to adsorb at least a portion of the $C_1$-$C_5$ hydrocarbon fraction and withdrawing a second adsorption effluent stream comprising hydrogen;
   (d) heating at least a substantial portion of the second adsorption effluent to raise the temperature to a temperature sufficient to desorb at least a portion of the $C_6+$ hydrocarbon fraction, passing the heated portion to said first adsorption zone and withdrawing a first desorption effluent stream comprising at least a portion of the $C_6+$ hydrocarbon fraction; and
   (e) reducing the pressure in the second adsorption zone to a pressure sufficient to desorb at least a portion of the $C_1$-$C_5$ hydrocarbon fraction therefrom and withdrawing a second desorption effluent comprising at least a portion of the $C_1$-$C_5$ hydrocarbons fraction.

10. The process of claim 9 wherein the $C_1$-$C_5$ hydrocarbon fraction comprises methane and the $C_6+$ hydrocarbon fraction comprises benzene.

11. The process of claim 10 wherein the temperature in said first adsorption zone sufficient to adsorb benzene is from about 0-100° F.

12. The process of claim 11 wherein the temperature in said first adsorption zone efficient to adsorb benzene is from about 40-100° F.

13. The process of claim 11 wherein the temperature in said second adsorption zone sufficient to adsorb methane is from about 0-120° F.

14. The process of claim 10 wherein the temperature in said first adsorption zone sufficient to desorb benzene is from about 100-600° F.

15. The process of Claim 14 which comprises heating the second adsorption effluent stream to a temperature of about 100-350° F. prior to passing through said first adsorption zone.

16. The process of claim 14 which comprises heating the second adsorption effluent stream to a temperature of about 300-600° F. prior to passing through said first adsorption zone.

17. The process of claim 10 wherein the pressure in said second adsorption zone sufficient to adsorb methane is from about 100-1000 psia.

18. The process of claim 10 wherein the pressure in said second adsorption zone sufficient to desorb methane is from about 14.7 to 200 psia.

19. The process of claim 10 wherein the first desorption effluent comprises hydrogen and benzene.

20. The process of claim 19 wherein the second desorption effluent comprises methane.

21. The process of claim 9 wherein said hydrocarbon conversion process is a dealkylation process.

22. The process of claim 21 wherein the effluent stream comprises hydrogen, methane and benzene.

23. The process of claim 22 which comprises passing a primary feedstream comprising toluene and hydrogen to a dealkylation reaction zone at conditions effective to form benzene and methane and withdrawing the effluent stream.

24. The process of claim 23 wherein the conditions include a temperature of from about 1100 to 1500° F. and a pressure of from about 300 to 800 psig.

25. The process of claim 23 wherein the conditions include a temperature of from about 900 to 1500°F. and a pressure of from about 300 to 1000 psig.

26. The process of claim 25 wherein and said dealkylation reaction zone comprises a dealkylation catalyst.

27. The process of claim 23 which comprises combining a hydrogen make-up stream with the first adsorption effluent stream prior to said passage to the second adsorption zone, said hydrogen make-up stream comprising hydrogen and light hydrocarbons.

28. The process of claim 9 wherein said hydrocarbon conversion process is a dehydrocyclodimerization process.

29. The process of claim 28 wherein the effluent stream comprises hydrogen, methane, ethane, propane, butane, and aromatic hydrocarbons.

30. The process of claim 29 which comprised passing a primary feedstream comprising propane and butane to a dehydrocyclodimerization reaction zone at conditions effective to form aromatic hydrocarbons and withdrawing the effluent stream.

31. The process of claim 30 wherein said dehydrocyclodimerization reaction zone contains a dehydrocyclodimerization catalyst.

32. The process of claim 31 wherein said conditions include a temperature of from about 920 to 1050° F. and a pressure below about 100 psig.

33. The process of claim 32 which comprises adsorbing a substantial portion of the aromatic hydrocarbons, propane and butane in said first adsorption zone to provide a first adsorption zone effluent stream comprising hydrogen, methane and ethane, and adsorbing a substantial portion of the methane and ethane in the second adsorption zone.

34. A hydrocarbon conversion process comprising:
(a) passing a reactor feed comprising feed hydrocarbons and a recycle stream as hereinafter characterized, to a reaction zone maintained at effective conditions to convert the feed hydrocarbons to product hydrocarbons, said product hydrocarbons having a different chemical composition than the feed hydrocarbons and having a $C_1$-$C_5$ hydrocarbon fraction and a $C_6+$ hydrocarbon fraction, and withdrawing a reactor product comprising hydrogen and the product hydrocarbons;
(b) passing at least a portion of the reactor product through a first adsorption zone containing solid adsorbent at a temperature sufficient to adsorb at least a portion of the $C_6+$ hydrocarbon fraction and withdrawing a first adsorption effluent stream comprising hydrogen and at least a portion of the $C_1$-$C_5$ hydrocarbons fraction;
(c) passing the first adsorption effluent stream through a second adsorption zone containing solid adsorbent at a pressure sufficient to adsorb at least a portion of the $C_1$-$C_5$ hydrocarbon fraction and withdrawing a second adsorption effluent stream comprising hydrogen;
(d) heating at least a substantial portion of the second adsorption effluent to a temperature sufficient to desorb at least a portion of the $C_6+$ hydrocarbon fraction, passing the heated portion to said first adsorption zone and withdrawing a first desorption effluent stream comprising hydrogen and at least a portion of the $C_6+$ hydrocarbon fraction;
(e) reducing the pressure in the second adsorption zone to a pressure sufficient to desorb at least a portion of the $C_1$-$C_5$ hydrocarbon fraction therefrom and withdrawing a second desorption effluent comprising at least a portion of the $C_1$-$C_5$ hydrocarbon fraction; and
(f) passing a portion of the first desorption effluent stream to the reaction zone to comprise the recycle stream.

35. The process of claim 34 wherein the hydrocarbon conversion process is a dealkylation process, the feed hydrocarbons comprise toluene, the product hydrocarbons comprise benzene and methane and the recycle stream comprises hydrogen.

36. The process of claim 34 wherein the hydrocarbon conversion process is a dehydrocyclodimerization process, the feed hydrocarbons comprise propane and butane, the product hydrocarbons comprise methane, ethane, propane, butane and aromatic hydrocarbons, and the recycle stream comprises propane and butane.

37. The process of claim 1 wherein the heated portion in step (c) comprises substantially the entire second adsorption effluent.

38. The process of claim 9 wherein the heated portion in step (d) comprises substantially the entire second adsorption effluent.

39. The process of claim 34 wherein the heated portion in step (d) comprises substantially the entire second adsorption effluent.

* * * * *